(12) United States Patent
Nguyen et al.

(10) Patent No.: US 7,195,755 B2
(45) Date of Patent: Mar. 27, 2007

(54) COMPOSITIONS COMPRISING AT LEAST ONE HYDROXIDE COMPOUND AND AT LEAST ONE REDUCING AGENT, AND METHODS FOR RELAXING HAIR

(75) Inventors: Nghi Van Nguyen, Edison, NJ (US); David W. Cannell, Plainfield, NJ (US)

(73) Assignee: L'Oreal S.A., Paris (FR)

(*) Notice: Subject to any disclaimer, the term of this patent is extended or adjusted under 35 U.S.C. 154(b) by 317 days.

(21) Appl. No.: 09/931,912

(22) Filed: Aug. 20, 2001

(65) Prior Publication Data
US 2003/0033677 A1    Feb. 20, 2003

(51) Int. Cl.
*A61Q 5/04*    (2006.01)

(52) U.S. Cl. ........... 424/70.2; 424/70.4; 424/70.51; 424/70.14; 424/70.23; 424/70.24

(58) Field of Classification Search ......... 424/70.2, 424/70.4, 70.5, 70.51, 70.14, 70.23, 70.24
See application file for complete search history.

(56) References Cited

U.S. PATENT DOCUMENTS

| | | | |
|---|---|---|---|
| 2,405,166 A | 8/1946 | Reed et al. ................ 133/31 |
| 2,464,280 A | 3/1949 | Reed et al. ............... 167/87.1 |
| 2,464,281 A | 3/1949 | Peterson ................... 167/87.1 |
| 2,564,722 A | 8/1951 | Reed et al. .................... 132/7 |
| 2,719,814 A | 10/1955 | Haefele .................... 167/87.1 |
| 3,017,328 A | 1/1962 | Childrey, Jr. et al. ..... 167/87.1 |
| 3,066,077 A | 11/1962 | De Mytt et al. .......... 167/87.1 |
| 3,242,052 A | 3/1966 | Sheffner ................... 132/204 |
| 3,243,346 A | 3/1966 | Bechmann et al. .......... 167/87 |
| 3,252,866 A | 5/1966 | Sheffner ................... 167/87.1 |
| 3,533,417 A | 10/1970 | Bartoszewicz et al. ....... 132/7 |
| 3,654,936 A | 4/1972 | Wajaroff ...................... 132/7 |
| 3,908,672 A | 9/1975 | Bore et al. .................... 122/7 |
| 3,971,391 A * | 7/1976 | Bore et al. .................... 132/7 |
| 3,973,574 A | 8/1976 | Minagawa et al. ........... 132/7 |
| 4,139,610 A | 2/1979 | Miyazaki et al. ............ 424/72 |
| 4,153,681 A | 5/1979 | Shiba ........................... 424/72 |
| 4,175,572 A | 11/1979 | Hsiung et al. ................ 132/7 |
| 4,218,435 A | 8/1980 | Shiba ........................... 424/72 |
| 4,237,910 A | 12/1980 | Khahil et al. ............... 424/72 |
| 4,272,517 A | 6/1981 | Yoneda et al. ............... 424/72 |
| 4,303,085 A | 12/1981 | de la Guardia et al. ....... 132/7 |
| 4,304,244 A | 12/1981 | de la Guardia ............... 132/7 |
| 4,314,572 A | 2/1982 | de la Guardia et al. ....... 132/7 |
| 4,322,401 A | 3/1982 | Harada ........................ 424/72 |
| 4,324,263 A | 4/1982 | de la Guardia ............... 132/7 |
| 4,361,157 A | 11/1982 | James ........................... 132/7 |
| 4,373,540 A | 2/1983 | de la Guardia ............. 424/89 |
| 4,390,033 A | 6/1983 | Khalil et al. ................. 132/7 |
| 4,416,296 A | 11/1983 | Meyers ......................... 132/7 |
| 4,424,820 A | 1/1984 | Cannell et al. ............... 132/7 |
| 4,509,983 A | 4/1985 | Szabo et al. ............. 106/38.2 |
| 4,605,018 A | 8/1986 | de la Guardia et al. ....... 132/7 |
| 4,783,395 A | 11/1988 | Hsieh et al. ................ 430/331 |
| 4,793,994 A * | 12/1988 | Helioff et al. ............. 424/70.4 |
| 4,816,246 A * | 3/1989 | Mathews et al. |
| 4,859,459 A | 8/1989 | Greiche et al. ............... 424/71 |
| 4,895,722 A | 1/1990 | Abe et al. ..................... 424/71 |
| 4,898,726 A | 2/1990 | Beste ............................ 424/72 |
| 4,950,485 A | 8/1990 | Akhtar et al. ................ 424/71 |
| 4,956,175 A | 9/1990 | Maignan et al. ............. 424/72 |
| 4,992,267 A | 2/1991 | DenBeste et al. ............ 424/71 |
| 5,015,767 A | 5/1991 | Maignan et al. ............ 564/181 |
| 5,077,042 A | 12/1991 | Darkwa et al. ............... 424/71 |
| 5,106,612 A | 4/1992 | Maignan et al. ............. 424/72 |
| 5,154,918 A | 10/1992 | Maignan et al. ............. 427/72 |
| 5,223,252 A | 6/1993 | Kolc et al. ................... 424/72 |
| 5,294,230 A | 3/1994 | Wu et al. ................. 8/127.51 |
| 5,332,471 A | 7/1994 | Naddeo et al. ................ 162/6 |
| 5,332,570 A | 7/1994 | Bergstrom et al. ........... 424/72 |
| 5,348,737 A | 9/1994 | Syed et al. .................... 424/71 |
| 5,376,364 A | 12/1994 | Darkwa et al. ............ 424/70.2 |
| 5,419,895 A | 5/1995 | Kubo et al. .............. 424/70.51 |
| 5,523,078 A | 6/1996 | Baylin ........................ 424/70.1 |
| 5,565,192 A | 10/1996 | Leroy et al. ............... 424/70.5 |
| 5,565,216 A | 10/1996 | Cowsar et al. ............. 424/70.4 |
| 5,591,425 A | 1/1997 | Dhaliwal ................... 424/70.4 |
| 5,609,859 A | 3/1997 | Cowsar ...................... 424/70.4 |
| 5,628,991 A | 5/1997 | Samain et al. ............. 424/70.1 |
| 5,637,295 A | 6/1997 | Lang et al. ................. 424/70.2 |
| 5,641,477 A | 6/1997 | Syed et al. ................. 424/70.4 |
| 5,679,327 A | 10/1997 | Darkwa et al. ............ 424/70.5 |
| 5,679,332 A | 10/1997 | Braun et al. ............... 424/70.2 |
| 5,725,848 A | 3/1998 | Borish et al. .............. 424/70.5 |
| 5,753,215 A | 5/1998 | Mougin et al. .............. 424/401 |
| 5,775,342 A | 7/1998 | Hohenstein et al. ........ 132/204 |
| 5,824,295 A | 10/1998 | Syed et al. ................. 424/70.4 |
| 5,833,966 A | 11/1998 | Samain ...................... 424/70.2 |
| 5,849,277 A | 12/1998 | Cowsar ...................... 424/70.4 |
| 5,872,111 A * | 2/1999 | Au et al. ........................ 514/62 |
| 5,932,201 A | 8/1999 | de Labbey et al. ...... 424/70.17 |

(Continued)

FOREIGN PATENT DOCUMENTS

CN    1138450    12/1996

(Continued)

OTHER PUBLICATIONS

S. Ogawa et al. A curing method for permanent hair straightening using thioglycolic and dithiodiglycolic acids, *Journal of Cosmetic Science*, 51, 379-399 (Nov./Dec. 2000).

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

Compositions, optionally heat-activated, methods and kits for lanthionizing keratinous fibers to achieve relaxation of said keratinous fibers comprising applying to keratinous fibers a composition comprising at least one hydroxide compound and at least one reducing agent chosen from thiols, sulfites, and derivatives thereof, and heating the keratinous fibers.

40 Claims, No Drawings

U.S. PATENT DOCUMENTS

| | | | | |
|---|---|---|---|---|
| 5,935,558 | A | 8/1999 | Malle | 424/70.1 |
| 5,961,667 | A | 10/1999 | Doehling et al. | 8/408 |
| 6,058,943 | A | 5/2000 | Davis-Harris | 132/205 |
| 6,287,582 | B1 | 9/2001 | Gott et al. | 424/402 |
| 6,435,193 | B1 | 8/2002 | Cannell et al. | 132/203 |
| 6,782,895 | B2 | 8/2004 | Van Nguyen et al. | 132/203 |
| 6,792,954 | B2 | 9/2004 | Cannell et al. | 132/203 |
| 2001/0008630 | A1* | 7/2001 | Pyles et al. | 424/400 |
| 2002/0189027 | A1 | 12/2002 | Cannell et al. | 8/405 |

FOREIGN PATENT DOCUMENTS

| | | |
|---|---|---|
| DE | 20 14 628 | 10/1971 |
| DE | 28 23 243 | 11/1979 |
| DE | 35 19 463 A1 | 12/1986 |
| DE | 43 26 974 A1 | 5/1994 |
| EP | 0 354 835 A1 | 2/1990 |
| EP | 0 465 342 A1 | 1/1992 |
| EP | 0 512 879 A2 | 11/1992 |
| EP | 0 636 358 A1 | 2/1995 |
| EP | 0 667 141 A2 | 8/1995 |
| EP | 0 712 623 A2 | 5/1996 |
| EP | 0 714 654 A1 | 6/1996 |
| EP | 0 726 251 A1 | 8/1996 |
| GB | 1 002 889 | 9/1965 |
| GB | 1 281 662 | 7/1972 |
| JP | A S50-029756 | 3/1975 |
| JP | A S50-029757 | 3/1975 |
| JP | A S63-190814 | 8/1988 |
| JP | A H02-104515 | 4/1990 |
| JP | A H04-243860 | 8/1992 |
| JP | A H04-295413 | 10/1992 |
| JP | A H5-39211 | 2/1993 |
| JP | A H05-246827 | 9/1993 |
| JP | A H6-172141 | 6/1994 |
| JP | A H6-343511 | 12/1994 |
| JP | A H7-101840 | 4/1995 |
| JP | A H08-245559 | 9/1996 |
| JP | A 2002-003346 | 1/2002 |
| JP | A 2002-68976 | 3/2002 |
| WO | WO 87/05500 | 9/1987 |
| WO | WO 89/06122 A | 7/1989 |
| WO | WO 93/01791 A | 2/1993 |
| WO | WO 97/07775 | 3/1997 |
| WO | WO 99/18922 | 4/1999 |
| WO | WO 01/64171 A2 | 9/2001 |
| WO | WO 01/74318 A2 | 10/2001 |
| WO | WO 02/067875 A1 | 9/2002 |

OTHER PUBLICATIONS

Co-pending U.S. Appl. No. 09/789,667—Title: Hair Relaxer Compositions Comprising at Least One Hydroxide Compound and at Least One Activating Agent, and Methods of Using the Same, Inventors: David W. Cannell et al., U.S. filing date Feb. 22, 2001.
Co-pending U.S. Appl. No. 09/516,942—Title: Hair Relaxer Compositions Utilizing Complexing Agent Activators, Inventors: Nghi Van Nguyen et al., U.S. filing date Mar. 1, 2000.
Co-pending U.S. Appl. No. 09/931,919—Title: Method for Relaxing and Re-Waving Hair Comprising at Least One Reducing Agent and at Least One Hydroxide Compound Inventors: David W. Cannell et al. U.S. filing date Apr. 20, 2001.
Co-pending U.S. Appl. No. 09/838,197—Title: Composition and Methods for Lanthionizing Keratin Fibers Using at Least One Organic Nucleophile and at Least One Hydroxide Ion Generator, Inventors: David W. Cannell et al. U.S. filing date: Apr. 20, 2001.
Co-pending U.S. Appl. No. 09/717,206—Title: Hair Relaxer Compositions Utilizing Cation Exchange Compositions Inventors: David W. Cannell et al. U.S. filing date: Nov. 22, 2001.
Co-pending U.S. Appl. No. 09/931,914—Title: Compositions Comprising at Least One Hydroxide Compound and at Least One Complexing Agent, and Methods for Using the Same Inventors: Nghi Van Nguyen et al. U.S. filing date: Aug. 20, 2001.
Co-pending U.S. Appl. No. 09/931,913—Title: Compositions Comprising at Least One Hydroxide Compound and at Least One Oxidizing Agent, and Methods to Straighten Curly Hair Inventors: Nghi Van Nguyen et al. U.S. filing date: Aug. 20, 2001.
International Search Report in PCT/US 02/21849 dated May 26, 2003.
BASF Corporation on-line catalog http://www.basf.com/businesses/consumer/cosmeticingredients/pdfs/ethnic_haircare.pdf.
Clariant, "Tylose Water-soluble cellulose ethers", Product range and fields of Application.
English language Derwent Abstract for DE 20 14 628.
English language Derwent Abstract for DE 28 23 243.
English language Derwent Abstract for DE 35 19 463.
English language Derwent Abstract for DE 43 26 974.
English language Derwent Abstract for EP 0 465 342.
English language Derwent Abstract for JP 60021704.
English language Derwent Abstract for JP 76-09013.
Examiner's Answer dated Jun. 13, 2005, in co-pending U.S. Appl. No. 09/838,197.
International Search Report for International Application No. PCT/US01/43193, Jul. 5, 2002, Examiner Simon.
International Search Report for International Application No. PCT/US02/03392, May 8, 2002, Examiner Bertrand.
International Search Report for International Application No. PCT/US02/08270, Aug. 7, 2002, Ex. Bertrand.
International Search Report for International Application No. PCT/US02/21846, Nov. 8, 2002, Ex. Marie.
International Search Report for International Application No. PCT/US02/21848, Nov. 25, 2002, Examiner Bertrand.
Office Action dated Apr. 13, 2004, in co-pending U.S. Appl. No. 09/931,913.
Office Action dated Apr. 28, 2003, in co-pending U.S. Appl. No. 09/931,914 (issued as U.S. Patent No. 6,782,895).
Office Action dated Apr. 12, 2005, in co-pending U.S. Appl. No. 09/789,667.
Office Action dated Aug. 6, 2003, in co-pending U.S. Appl. No. 09/838,197.
Office Action dated Dec. 16, 2003, in co-pending U.S. Appl. No. 10/214,942 (Now issued as U.S. Patent No. 6,792,954).
Office Action dated Feb. 6, 2003, in co-pending U.S. Appl. No. 09/838,197.
Office Action dated Feb. 5, 2003, in co-pending U.S. Appl. No. 09/789,667.
Office Action dated Jul. 22, 2004, in co-pending U.S. Appl. No. 09/838,197.
Office Action dated Jul. 23, 2004, in co-pending U.S. Appl. No. 09/931,913.
Office Action dated Jul. 26, 2004, in co-pending U.S. Appl. No. 09/789,667.
Office Action dated Jul. 31, 2003, in co-pending U.S. Appl. No. 09/789,667.
Office Action dated Nov. 19, 2004, in co-pending U.S. Appl. No. 09/931,913.
Office Action dated Oct. 27, 2003, in co-pending U.S. Appl. No. 09/931,913.
Office Action dated Sep. 9, 2003, in co-pending U.S. Appl. No. 09/931,914 (issued as U.S. Patent No. 6,782,895).
Office Action dated Sep. 10, 2002, in co-pending U.S. Appl. No. 09/789,667.
Robbins, Clarence R., "Chemical and physical behavior of human hair," pp. 124-126, 148-151, and 162-163, Springer (2002).
Schoon, Douglas D., "Hair structure and chemistry simplified", Revised edition, pp. 191-192, Milady Publishing Co. (1993).
Zahn, Helmut, "N,O-Peptidyl shift, disulfide exchange, and lanthionine formation in wool and other proteins containing cystine," Chimia (Switz.) (1961), 15, 378-94.
Zviak, C., The Science of Hair Care, pp. 185-186 (1986).
Advisory Action dated Jul. 22, 2005, in co-pending U.S. Appl. No. 09/789,667.
English language Derwent Abstract for CN 1138450.
English language Derwent Abstract for JP-A H6-172141.

English language Derwent Abstract for JP-A H7-101840.
English language Derwent Abstract for JP-A 2002-003346.
English language Derwent Abstract for JP-A 2002-68976.
Hair Science: Japan Hair Science Assoc., Jan. 10, 1996, 2nd. Ed., p. 87.
English language translation of Hair Science: Japan Hair Science Assoc., Jan. 10, 1996, 2nd. Ed., p. 87.
Office Action dated Aug. 31, 2005, in co-pending U.S. Appl. No. 09/931,913.

* cited by examiner

COMPOSITIONS COMPRISING AT LEAST ONE HYDROXIDE COMPOUND AND AT LEAST ONE REDUCING AGENT, AND METHODS FOR RELAXING HAIR

The present invention relates to compositions and methods for lanthionizing keratinous fibers to achieve relaxation of the keratinous fibers using a combination of at least one hydroxide compound and at least one reducing agent chosen from thiols, sulfites, and derivatives thereof.

Straightening or relaxing the curls of very curly hair may increase the manageability and ease of styling of such hair. In today's market, there is an increasing demand for the hair care products referred to as "hair relaxers," which can relax or straighten naturally curly or kinky hair. Hair relaxers may either be applied in a hair salon by a professional or in the home by the individual consumer.

Hair fiber, a keratinous material, comprises proteins (polypeptides). Many of the polypeptides in hair fibers are bonded together or cross-linked with disulfide bonds (—S—S—). A disulfide bond may be formed from the reaction of two sulfhydryl groups (—SH), one on each of two cysteine residues, which results in the formation of a cystine residue. A cystine residue comprises a cross-link of the formula —$CH_2$—S—S—$CH_2$— between 2 polypeptides. While there are other types of bonds which occur between the polypeptides in hair fibers, such as ionic (salt) bonds, the permanent curling or the shape of the hair is essentially dependent on the disulfide bonds of cystine residues.

Generally, hair relaxing processes are chemical processes which may alter the aforementioned disulfide bonds between polypeptides in hair fibers and may form lanthionine residues [S[$CH_2$CH(NH—)(CO—)]$_2$]. Thus, the term "lanthionizing" is used when one skilled in the art refers to the relaxing or straightening of keratinous fibers by hydroxide ions.

For example, hair fibers may be relaxed or straightened by disrupting the disulfide bonds of the hair fibers with an alkaline reducing agent. The chemical disruption of disulfide bonds with such an agent is generally combined with mechanical straightening of the hair, such as combing, and straightening generally occurs due to changes in the relative positions of neighboring polypeptide chains within the hair fiber. This reaction is generally terminated by rinsing and/or application of a neutralizing composition.

The reaction with the alkaline agent is normally initiated by available hydroxide ions. As used herein, "available hydroxide ions" are hydroxide ions which are available for lanthionization. Not to be limited by theory, there are two reaction sequences that are predominantly used in the art to explain the disruption of the disulfide bonds in hair fibers by available hydroxide ions. Both of these reaction sequences result in lanthionine residue formation. One reaction sequence comprises at least one bimolecular nucleophilic substitution reaction wherein an available hydroxide ion directly attacks the disulfide linkage of a cystine residue. The result is the formation of lanthionine residues and HOS$^-$. See Zviak, C., *The Science of Hair Care*, pp. 185–186 (1986). The second reaction sequence comprises at least one β-elimination reaction initiated by the nucleophilic attack of an available hydroxide ion on a hydrogen atom bonded to a carbon atom that is in the β-position with respect to the disulfide bond of a cystine residue. Id. The result is the formation of a dehydroalanine residue. The dehydroalanine residue then reacts with either the thiol group of a cysteine residue or the amino group of an alanine residue to form a lanthionine residue or a lysinoalanine residue, respectively. These stable irreversible crosslinks in the treated hair make subsequent chemical re-linking of the polypeptides unnecessary. Thus, the only step that may be required following a straightening process using such hydroxide-containing alkaline agents is the removal of any excess alkaline solution to avoid and/or minimize damage to the hair protein or skin. If such a step is required, an acidic shampoo may be used to neutralize residual alkali and remove it from the hair and scalp.

Hydroxide-containing alkaline agents also have other advantages. For example, alkaline agents, such as sodium hydroxide and guanidine hydroxide, do not have a highly objectionable odor or cause such an odor on treating the hair. Further, hydroxide-based straighteners generally have relatively fast processing times and good straightening of naturally curly or kinky hair. Additionally, the achieved straightening effect is more durable; i.e., less likely to revert to a curly state after shampooing and exposure to elements than is hair straightened with some other straighteners.

Despite these advantages, certain hydroxide-containing alkaline agents may have disadvantages. These disadvantages may be heightened when the hydroxide-containing alkaline agent is sodium hydroxide. Specifically, the causticity of sodium hydroxide can adversely affect the condition of the hair, for example, leaving it in a brittle state and harsh to the touch. Additionally, prolonged or unnecessary exposure of hair to such a strong alkali can weaken, break and dissolve the hair. In some instances, such a strong alkali can discolor the natural color of the hair. For example, the tone of natural brown hair may be reddened and natural white or grey hair may be yellowed. Further, the natural sheen of the hair may be delustered.

Most frequently, commercial relaxing compositions are in the form of gels or emulsions that contain varying proportions of strong water-soluble bases, such as sodium hydroxide (NaOH), or of compositions that contain slightly-soluble metal hydroxides, such as calcium hydroxide (Ca(OH)$_2$), which can be converted in situ to soluble bases, such as guanidine hydroxide. Traditionally, the two main hair relaxers used in the hair care industry for generating hydroxide ions are referred to as "lye" (lye=sodium hydroxide) relaxers and "no lye" relaxers.

The "lye" relaxers generally comprise sodium hydroxide in a concentration ranging from 1.5% to 2.5% by weight relative to the total weight of the composition (0.38M–0.63 M) depending on the carrier used, the condition of the hair fibers and the desired length of time for the relaxation process.

While "no lye" relaxers may not contain lye, they may nonetheless rely on the soluble hydroxides of inorganic metals, such as potassium hydroxide and lithium hydroxide. Other "no lye" relaxers may use hydroxide ions obtained, for example, from a slightly-soluble source, such as Ca(OH)$_2$. For example, the slightly soluble Ca(OH)$_2$ may be mixed with guanidine carbonate to form guanidine hydroxide, a soluble but unstable source of hydroxide, and insoluble calcium carbonate (CaCO$_3$). This reaction is driven to completion by the precipitation of CaCO$_3$ and is, in effect, substituting one insoluble calcium salt for a slightly soluble calcium salt. Because guanidine hydroxide is unstable, the components are stored separately until the time of their use.

Reducing agents, such as compounds comprising at least one thiol group, may also relax or straighten hair by disrupting disulfide bonds of the hair fibers. More commonly, reducing agents, such as thioglycolates, sulfites, cysteines and their derivatives, are used for texturizing purposes in hair straightening or relaxing compositions. Processes comprising the application of these reducing agents generally require two steps: (1) a reducing step comprising the use of the reducing agent, and (2) a neutralizing step comprising the use of an oxidizing composition.

These reducing agents may have disadvantages not present with alkaline agents. For example, thiol-based straightening or relaxing may require the use of an oxidizing neutralizer, such as hydrogen peroxide, to chemically relink the hair keratin disulfide bonds and stop the straightening process quickly. As the thiol-reduced hair is in an alkaline state, any excess neutralizer must also be removed to avoid bleaching the natural color of the hair.

The reaction with the reducing agent is normally initiated by thiolate ions. Generally, the higher the concentration of the thiolate ions in the composition, the faster the straightening or relaxing reaction will occur. See Zviak at page 190. This concentration, and therefore the rate of the reaction, is dependent on the ionization constant $K_i$ of the thiol used. Thus, the pK value of a particular thiol expresses the nature of the thiol and determines both the equilibrium level and, therefore, the concentration of thiolate ions at a given pH. For example, reducing agents are generally used in a concentration of about 5% at a pH ranging from 9 to 10. As with hydroxide-containing alkaline agents, a high concentration of reducing agent may result in hair damage, and a low concentration may result in reversion of the hair to its original curly state (i.e., non-durable relaxation).

Some strides have been made to improve the condition of sodium hydroxide-straightened hair by incorporating an auxiliary hair keratin disulfide reducing agent having a sulfhydryl functional group available chosen from cysteine, homologs of cysteine, and water soluble derivatives of cysteine. See, for example, U.S. Pat. No. 4,992,267, the disclosure of which is incorporated herein by reference. This patent discloses the use of sodium hydroxide at concentrations of between about 1 weight percent to about 2.5 weight percent, preferably between about 1.5 weight percent and about 2.25 weight percent relative to the total concentration of the composition.

Further, co-pending U.S. patent application Ser. No. 09/789,667, the disclosure of which is incorporated herein by reference, discloses compositions, and methods for using these compositions, for lanthionizing keratinous fibers comprising at least one hydroxide compound with the proviso that the at least one hydroxide compound is not sodium hydroxide, lithium hydroxide or potassium hydroxide and at least one activating agent chosen from cysteine-based compounds. These compositions may make it possible to decrease the amount of the at least one hydroxide compound needed even further while maintaining good hair condition.

The use of both reducing agents and hydroxide-based compounds has previously been disclosed. A curing method for permanent hair straightening using thioglycolic acid, dithioglycolic acid, and potassium hydroxide is known. See Ogawa, S. et al., *J. Cosmet. Sci.*, 51, 379–399 (2000). This method comprises three steps: (1) reduction using thioglycolic acid (3% to 9%), dithioglycolic acid, potassium hydroxide (1.05%), EDTA and monoethanolamine; (2) heat treatment, followed by (3) oxidation of the hair. Further for example, a process for imparting smoothness, body and a permanent wave pattern is also known. See U.S. Pat. No. 6,058,943. This process comprises at least eleven steps such as applying an aqueous alkaline relaxant composition containing an alkaline hydroxide reducing agent to the hair (step "(a)"), applying an aqueous waving composition containing a thioglycolate reducing agent to the hair (step "(d)"), and shampooing and rinsing the hair with a neutralizing shampoo and water (step "(h)").

The present invention may relax or straighten keratinous fibers without damage to the fibers but at the same time without substantial reversion to the original curly state of the hair using compositions comprising low concentrations of at least one hydroxide compound and of at least one reducing agent.

Thus, the present invention, in one aspect, provides a composition for lanthionizing keratinous fibers to achieve relaxation of the keratinous fibers comprising (i) at least one hydroxide compound and (ii) at least one reducing agent chosen from thiols, sulfites, and derivatives thereof, wherein the at least one hydroxide compound and the at least one reducing agent are present in a combined amount effective to relax keratinous fibers, and with the proviso that if the at least one reducing agent is chosen from cysteine, cysteine derivatives, and thioglycolic acid, then the at least one hydroxide compound is present in an amount such that the amount of hydroxide ion is less than 1% by weight relative to the total weight of the composition. In one embodiment, the composition is heat-activated.

In another aspect, the present invention provides a composition for lanthionizing keratinous fibers to achieve relaxation of the keratinous fibers comprising (i) at least one hydroxide compound and (ii) at least one reducing agent chosen from thiols, sulfites, and derivatives thereof, wherein the at least one hydroxide compound is present in an amount such that the amount of hydroxide ion ranges from 0.1% to 1% by weight relative to the total weight of the composition. In one embodiment, the composition is heat-activated.

In another aspect of the invention, the present invention provides a method for lanthionizing keratinous fibers to achieve relaxation of the keratinous fibers comprising: (i) generating hydroxide ions in at least one solvent, wherein said step of generating comprises combining in the at least one solvent at least one hydroxide compound and at least one reducing agent chosen from thiols, sulfites, and derivatives thereof; (ii) applying a composition comprising the generated hydroxide ions to keratinous fibers for a sufficient period of time to lanthionize the keratinous fibers; and (iii) heating the keratinous fibers, wherein the at least one hydroxide compound and the at least one reducing agent are present in a combined amount effective to relax keratinous fibers, further wherein the composition is applied prior to or during heating, and with the proviso that the method does not comprise an oxidation treatment subsequent to the heating.

In yet another aspect of the invention, the present invention provides a method for lanthionizing keratinous fibers to achieve relaxation of the keratinous fibers comprising: (i) generating hydroxide ions in at least one solvent, wherein said step of generating comprises combining in the at least one solvent at least one hydroxide compound and at least one reducing agent chosen from thiols, sulfites, and derivatives thereof; (ii) applying a composition comprising the generated hydroxide ions to keratinous fibers for a sufficient period of time to lanthionize the keratinous fibers; and (iii) heating the keratinous fibers, wherein the at least one hydroxide compound and the at least one reducing agent are present in a combined amount effective to relax keratinous fibers, further wherein the composition is applied prior to or during the heating, and with the proviso that if the at least one reducing agent is thioglycolic acid, the at least one hydroxide compound is present in an amount less than 1% by weight relative to the total weight of the composition. The lanthionization is terminated when a desired level of relaxation of the keratinous fibers has been reached. This method may optionally further comprise other treatments, such as oxidation treatments.

Further, the invention also provides for a multicomponent kit for lanthionizing keratinous fibers, wherein the kit comprises at least two components. A first component of the kit comprising at least one hydroxide compound, and a second component comprising at least one reducing agent chosen from thiols, sulfites, and derivatives thereof.

Certain terms used herein are defined below:

As used herein, "at least one" means one or more and thus includes individual components as well as mixtures/combinations.

"Keratinous fibers" as defined herein may be human keratinous fibers, and may be chosen from, for example, hair.

"Heating" refers to the use of elevated temperature (i.e. above 100° C.). In one embodiment, the heating in the inventive method may be provided by directly contacting the keratinous fibers with a heat source, e.g., by heat styling of the keratinous fibers. Non-limiting examples of heat styling by direct contact with the keratinous fibers include flat ironing, and curling methods using elevated temperatures (such as, for example, setting hair in curlers and heating, and curling with a curling iron and/or hot rollers). In another embodiment, the heating in the inventive method may be provided by heating the keratinous fibers with a heat source which may not directly contact the keratinous fibers. Non-limiting examples of heat sources which may not directly contact the keratinous fibers include blow dryers, hood dryers, heating caps and steamers.

"A heat-activated" composition, as used herein, refers to a composition which relaxes keratinous fibers better than the same composition which is not heated during or after application of the composition.

"Lanthionizing," as used herein, refers to the formation of at least one lanthionine residue, which may accomplish, for example, any level of relaxation.

"Relaxation," and "relaxing," as used herein, include any level of relaxing, for example, from a slight relaxing to straightening.

It is to be understood that both the foregoing general description and the following detailed description are exemplary and explanatory only and are not restrictive of the invention as claimed.

As described above, the lanthionization of keratinous fibers is believed to be driven by the disruption of the disulfide bonds of cystine residues in the fibers. The compositions and methods of the present invention may provide a novel way of generating sufficient available hydroxide ions from at least one hydroxide compound to effectively and relax and/or straighten the hair with lower concentrations of the at least one hydroxide compound and of at least one reducing agent. Such compositions may be capable of relaxing the keratinous fibers without damaging the fibers. This is particularly true when the compounds are applied to the hair, and then the hair is heated.

Thus, the present invention provides a composition for lanthionizing keratinous fibers to achieve relaxation of the keratinous fibers comprising (i) at least one hydroxide compound and (ii) at least one reducing agent chosen from thiols, sulfites, and derivatives thereof. The at least one hydroxide compound and the at least one reducing agent are present in a combined amount effective to relax keratinous fibers. If the at least one reducing agent is chosen from cysteine, cysteine derivatives, and thioglycolic acid, then the at least one hydroxide compound is present in an amount such that the amount of hydroxide ion is less than 1% by weight relative to the total weight of the composition. In one embodiment, the composition is heat-activated. In one embodiment, the composition further comprises a cation exchange composition. In another embodiment, the composition further comprises at least one complexing agent effective for dissociating the at least one hydroxide compound in sufficient quantity to effect lanthionization of the keratinous fibers.

The present invention also provides a composition for lanthionizing keratinous fibers to achieve relaxation of the keratinous fibers comprising (i) at least one hydroxide compound and (ii) at least one reducing agent chosen from thiols, sulfites, and derivatives thereof, wherein the at least one hydroxide compound is present in an amount such that the amount of hydroxide ion ranges from 0.1% to 1% by weight relative to the total weight of said composition. In one embodiment, the composition is heat-activated. In one embodiment, the composition further comprises a cation exchange composition. In another embodiment, the composition further comprises at least one complexing agent effective for dissociating the at least one hydroxide compound in sufficient quantity to effect lanthionization of the keratinous fibers.

The present invention also provides a method for lanthionizing keratinous fibers to achieve relaxation of the keratinous fibers comprising (i) generating hydroxide ions in at least one solvent comprising combining in the at least one solvent at least one hydroxide compound and at least one reducing agent chosen from thiols, sulfites, and derivatives thereof; (ii) applying a composition comprising the generated hydroxide ions to keratinous fibers for a sufficient period of time to relax the keratinous fibers; and (iii) heating the keratinous fibers. The at least one hydroxide compound and the at least one reducing agent are present in a combined amount effective to relax keratinous fibers. The at least one hydroxide compound may be added to a composition containing the at least one reducing agent, or vice versa. Further, the composition is applied prior to or during heating. In one embodiment, the composition is applied prior to and during heating. This method does not comprise an oxidation treatment subsequent to heating. The lanthionization is terminated when a desired level of relaxation of the keratinous fibers has been reached. In one embodiment, the composition further comprises a cation exchange composition. In another embodiment, the composition further comprises at least one complexing agent effective for dissociating the at least one hydroxide compound in sufficient quantity to effect lanthionization of the keratinous fibers.

In yet another embodiment, the present invention provides a method for lanthionizing keratinous fibers as described above but wherein the method may optionally further comprise other treatments, such as oxidation treatments, provided that if the at least one reducing agent is thioglycolic acid, then the at least one hydroxide compound is present in an amount such that the amount of hydroxide ion is less than 1% by weight relative to the total weight of the composition.

According to the present invention, the at least one hydroxide compound may be chosen from any compound comprising at least one hydroxide group which may at least partially dissociate into a counterion and a hydroxide ion in solution. Non-limiting examples of the at least one hydroxide compound include alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable. Other non-limiting examples of the at least one hydroxide compound include sodium hydroxide, potassium hydroxide, lithium hydroxide, rubidium hydroxide, cesium hydroxide, francium hydroxide, beryllium hydroxide, magnesium hydroxide, calcium hydroxide, strontium hydroxide, barium hydroxide, cupric hydroxide, molybdenum hydroxide, manganese hydroxide, zinc hydroxide, cobalt hydroxide, nickel hydroxide, cadmium hydroxide, gold hydroxide, lanthanum hydroxide, cerium hydroxide, actinium hydroxide, thorium hydroxide, aluminum hydroxide, guanidine hydroxides and quaternary ammonium hydroxides. The at least one hydroxide compound can also be chosen from those formed in situ, such as, for example, guanidine hydroxide. As previously mentioned, guanidine hydroxide may be formed in situ, for example, from the reaction of calcium hydroxide and guanidine carbonate.

According to the present invention, the at least one hydroxide compound may be present, for example, in an amount sufficient to effect relaxation of the keratinous fibers without damaging the fibers. According to one embodiment of the present invention, the at least one hydroxide compound is present in an amount such that the amount of hydroxide ion generally ranges from 0.05% to 3%, such as from 0.1% to 1% by weight relative to the total weight of the composition. As previously mentioned, in certain embodiments, if the at least one reducing agent is chosen from cysteine, cysteine derivatives, and thioglycolic acid, then the at least one hydroxide compound is present in an amount such that the amount of hydroxide ion is less than 1% by weight relative to the total weight of the composition.

The at least one reducing agent of the present invention is chosen from thiols, sulfites, and derivatives thereof. As used herein, derivatives include salts. Derivatives of thiols and of sulfites refers to thiols and sulfites, respectively, that are substituted with any substituent at any position of the molecule, provided that the reducing ability of the molecule is not substantially adversely affected. The applicability of a derivative, analog, etc. of a thiol or a sulfite may be evaluated, for example, using the procedures of Example 1. The at least one reducing agent may be chosen from thiols, sulfites and derivatives thereof, such as, for example, those listed in the *International Cosmetic Ingredient Dictionary and Handbook,* 8$^{th}$ Ed., Vol. 2 (2000) at page 1767. Non-limiting examples of suitable thiols are thioglycolates, thiolactates, thiolglycerols, thiocarboxylic acids, thioesters, thioamides, alkyl mercaptans, and cysteine. In one embodiment, the at least one reducing agent is chosen from thioglycolates, and in yet another embodiment, the at least one reducing agent is chosen from ammonium thioglycolate. Non-limiting examples of suitable sulfites are hydrogen sulfite, organic sulfites such as alkyl sulfites (such as dimethyl sulfite and diethyl sulfite) and alkylene sulfites (such as glycol sulfite, 1,2-propyleneglycol sulfite, and 1,3-butyleneglycol sulfite) and inorganic sulfites (such as ammonium sulfite, magnesium hydrogen sulfite, potassium sulfite, sodium sulfite, sodium hydrogen sulfite, silver sulfite, and zinc sulfite).

According to the present invention, the at least one reducing agent is generally present in an amount sufficient to complement the relaxing and/or straightening effects of the at least one hydroxide compound such that the at least one reducing agent and at least one hydroxide compound are present in a combined amount effective to relax the keratinous fibers. In one embodiment, the at least one reducing agent is present in an amount ranging from 0.1% to 5% by weight relative to the total weight of the composition. The aforementioned amounts were calculated based on ammonium thioglycolate as the at least one reducing agent. One of skill in the art may adjust the amounts according to the particular at least one reducing agent chosen.

According to the present invention, the at least one solvent can be chosen from solvents commonly used in compositions for keratinous fibers. Non-limiting examples of the at least one solvent include water and solvents which may lower the ionic bonding forces in the solute molecules enough to cause at least partial separation of their constituent ions, such as dimethyl sulfoxide (DMSO). In one embodiment, the at least one solvent is chosen from water and DMSO. The at least one solvent can be present in an amount sufficient to ensure that, upon mixing, enough of the generated available hydroxide ions remain soluble in order to effect lanthionization of keratinous fibers.

The compositions of the present invention as well as those used in the methods of the present invention may further comprise at least one suitable additive chosen from additives commonly used in hair relaxing compositions. Non-limiting examples of the at least one suitable additive include dyes, anionic surfactants, cationic surfactants, nonionic surfactants, amphoteric surfactants, fragrances, screening agents, preserving agents, proteins, vitamins, silicones, polymers such as thickening polymers, plant oils, mineral oils, synthetic oils and any other additive conventionally used in compositions for the care and/or treatment of hair.

Further, these compositions may further comprise at least one cation exchange composition which may be effective in participating in the lanthionizing process. In one embodiment, the at least one cation exchange composition is chosen from silicates. Non-limiting examples of silicates include aluminum silicates and silicates of alkali metals (such as analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate). Non-limiting examples of alkali metals are sodium, lithium, potassium and mixtures of any of the foregoing. In one embodiment, the at least one cation exchange composition is a clay. In another, silicates are chosen from zeolites, while in yet another embodiment, silicates are chosen from zeolite clays.

These compositions may further comprise at least one complexing agent effective for dissociating the at least one hydroxide compound in an amount sufficient to effect lanthionization of keratinous fibers. The at least one complexing agent may be an agent, such as a chelating agent or a sequestering agent, that leads to a partial or full dissociation of the at least one hydroxide compound. The at least one complexing agent may chelate, sequester or otherwise tie up the counter ion of the at least one hydroxide compound, allowing more available hydroxide ions to be liberated. Of course, the at least one complexing agent may do both. In any event, the net effect of the use of at least one complexing agent in accord with the present invention is the generation of enough available hydroxide ions to effect lanthionization of keratinous fibers without relying on precipitation of a counter ion, such as $Ca^{++}$ in the form of $CaCO_3$.

In the multicomponent kit of the present invention, for example, the at least one reducing agent may be formulated with the component comprising at least one hydroxide compound or with the component comprising at least one complexing agent or itself may be a third component that is combined with one or both of the component comprising at least one hydroxide compound and the component comprising at least one complexing agent.

In one embodiment, the at least one complexing agent of the present invention may be chosen from chelating agents, sequestering agents and salts of any of the foregoing. A chelating agent is a compound or ligand that can bind to a metal ion, usually through more than one ligand atom, to form a chelate. See Lewis, R. J., *Hawley's Condensed Chemical Dictionary* p. 240 (1997). A chelate is usually a type of coordination compound in which a central metal ion, such as $Co^{2+}$, $Ni^{2+}$, $Cu^{2+}$, $Ca^{2+}$ or $Zn^{2+}$, is attached by coordinate links to two or more nonmetal atoms, i.e., ligands, in the same molecule. Non-limiting examples of common chelating agents include ethylene-diaminetetraacetic acid (EDTA), nitrilotriacetic acid and ethylenegylcol-bis (β-amino-ethyl ether)-N,N-tetraacetic acid.

Sequestering agents may be chosen from any material that prevents at least one ion from exhibiting its usual properties due to close combination with that material. Id. Certain phosphates, for example, form a coordination complex with metal ions in solution so that the usual precipitation reactions may be prevented. Id. For example, calcium soap precipitates are not produced from hard water treated with certain phosphates, or metaphosphates. Id. Other non-limiting examples of sequestering agents include hydroxy carboxylic acids, such as gluconic acid, citric acid and tartaric acid. Id.

In addition, other non-limiting examples of chelating agents and sequestering agents include phosphonates, amino acids and crown ethers. In one embodiment, the at least one complexing agent is chosen from amino acids, such as monosodium glutamate, a known calcium chelator.

The at least one complexing agent may also be chosen from phosphates demonstrating chelating and/or sequestering properties and silicates demonstrating chelating and/or sequestering properties. Non-limiting examples of phosphates demonstrating chelating and/or sequestering properties include tripotassium phosphate and trisodium phosphate. Non-limiting examples of silicates demonstrating chelating and/or sequestering properties include disodium silicate and dipotassium silicate.

Further, the at least one complexing agent may also be chosen from organic acids and salts thereof. The cations that may be used to form the salts of organic acids of the present invention may be chosen from organic cations and inorganic cations. For example, in one embodiment, the inorganic cations are chosen from potassium, sodium and lithium. In another embodiment, for example, the organic cations are chosen from cations comprising ammonium groups (such as, for example, ammonium hydroxide) and cations comprising amino groups which may form ammonium groups. In another embodiment, the organic cations are chosen from guanidine, guanidine derivatives, and amine bases. In yet another embodiment, the at least one complexing agent is chosen from mono-hydroxycarboxylic acids, dihydroxycarboxylic acids, polyhydroxycarboxylic acids, mono-aminocarboxylic acids, di-aminocarboxylic acids, poly-aminocarboxylic acids, mono-hydroxysulfonic acids, di-hydroxysulfonic acids, polyhydroxysulfonic acids, mono-hydroxyphosphonic acids, dihydroxyphosphonic acids, polyhydroxyphosphonic acids, mono-aminophosphonic acids, diaminophosphonic acids and polyaminophosphonic acids.

In a further embodiment, the at least one complexing agent is chosen from ethylene diamine tetraacetic acid (EDTA), N-(hydroxyethyl) ethylene diamine triacetic acid, aminotrimethylene phosphonic acid, diethylenetriaminepentaacetatic acid, lauroyl ethylene diamine triacetic acid, nitrilotriacetic acid, iminodisuccinic acid, tartaric acid, citric acid, N-2-hydroxyethyliminodiacetic acid and salts of any of the foregoing.

In yet another embodiment, the at least one complexing agent is chosen from a salt of EDTA, such as sodium EDTA, lithium EDTA, potassium EDTA and guanidine EDTA. EDTA has a strong calcium binding constant over a wide range of pH. For example, tetrasodium EDTA generally solubilizes calcium hydroxide in aqueous media to give a clear solution. The use of at least one complexing agent, such as tetrasodium EDTA, that solubilizes the counter ion of the at least one hydroxide compound may offer the benefit of no "ashing." However, the use of one or more complexing agents that do not completely solubilize the counter ion but only form slightly-soluble or sparingly-soluble complexing agent-counter ion complexes is also within the practice of the invention.

In another embodiment, the at least one complexing agent may comprise at least one "soft" entity chosen from "soft" bases and "soft" cations and at least one anion chosen from chelating anions and sequestering anions. Non-limiting examples of "soft" cations include organic cations such as guanidine. Non-limiting examples of "soft" bases include amines such as monoethanolamine, diethanolamine and triethanolamine. Such a combination of at least one "soft" entity and at least one anion may be effective if the "soft" entity exists at a high enough pH to achieve straightening or relaxing of the hair fibers. For example, amino acids such as arginine may be used to neutralize EDTA to make a "soft" base/strong chelator pair.

Depending on the nature of the at least one complexing agent, the solubility of the complex formed between the at least one complexing agent and the counter ion of the at least one hydroxide compound in the reaction medium may vary. In one embodiment, the at least one complexing agent-counter ion complex is considered by one of ordinary skill in the art to be soluble in the reaction medium. In another embodiment, a composition of the invention provides for an at least one complexing agent-counter ion complex having a solubility in water of greater than 0.03% at 25° C. and at a pH of 7.0, such as greater than 1% at 25° C. and at a pH of 7.0.

As one of ordinary skill in the art would recognize, mixtures of complexing agents including mixtures of at least one chelating agent and at least one sequestering agent are also within the practice of the invention. In one embodiment, a less active chelating agent, such as pentasodium aminotrimethylene phosphonate, may be mixed with a more active chelating agent, such as EDTA, to achieve a desired lanthionization of keratinous fibers at a slower rate.

The compositions of the present invention may be provided as one-part compositions comprising at least one hydroxide compound, at least one reducing agent, and, optionally, at least one cation exchange resin and/or at least one complexing agent. Alternatively, the compositions may be provided in the form of a multicomponent kit. According to one embodiment of the present invention, the multicomponent kit for lanthionizing keratinous fibers may comprise at least two separate compartments. A first compartment of the kit may comprise a first composition containing at least one hydroxide compound. This first composition may be in a form chosen from an emulsion, solution, gel, cream, and paste. A second compartment of the kit can comprise at least one reducing agent, and, optionally, at least one complexing agent that is effective for dissociating the at least one hydroxide compound in sufficient quantity to effect lanthionization of keratinous fibers. This composition may be in a form chosen from an emulsion, suspension, solution, gel, cream, and paste. The first and/or the second compartments may further contain at least one cation exchange composition. The skilled artisan, based on the stability of the composition and the application envisaged, will be able to determine how the composition and/or multicomponent compositions should be stored and mixed.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and in the attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following example is intended to illustrate the invention without limiting the scope as a result. The percentages are given on a weight basis.

EXAMPLE

Relaxing Efficiency of Naturally Kinky Hair Treated with NaOH/thioglycolate

Compositions comprising from 0.1% to 1.0% NaOH (a hydroxide compound according to the present invention) and up to 5% ammonium thioglycolate (a reducing agent according to the present invention) were prepared as shown in Table 1. A naturally kinky hair swatch was either sprayed with the thioglycolate solution or was soaked in the thioglycolate solution and then blotted dry. A hot curling iron was used to pull the hair straight for 3–12 seconds. The hair swatch was rinsed and shampooed, and then placed in a humidity chamber at 90% Relative Humidity (% RH) for 24 hours. The percent Relaxing Efficiency (% RE) is defined as % $RE = (L_f/L_t) \times 100$ where $L_f$=length of the relaxed hair after 24 hours at 90% RH $L_t$=length of the hair at the straight configuration The greater the relaxing efficiency (% RE), the straighter the hair after treatment. The results are shown in Table 1.

TABLE 1

Relaxing Efficiency (% RE) After 24 hours under 90% relative Humidity of Hair Treated with Various Compositions

| Amount of Ammonium Thioglycolate | Amount of NaOH (%) | | | | |
|---|---|---|---|---|---|
| (%) | 0.1 | 0.3 | 0.5 | 0.7 | 1 |
| 0 | 10% | 18% | 25% | 36% | 50% |
| 0.1 | 30% | 78% | 80% | 82% | 86% |
| 0.5 | 30% | 86% | 88% | 89% | 94% |
| 1 | 44% | 90% | 93% | 95% | 97% |
| 2 | 53% | 93% | 94% | 96% | 97% |
| 5 | 54% | 96% | 96% | 98% | 98% |

A high relaxation efficiency after 24 hours under 90% relative humidity indicates that the hair did not display reversion. The data show that naturally curly hair can be effectively relaxed without substantial reversion after being treated with solutions containing low concentrations of NaOH and thioglycolate and then subjected to heat.

What is claimed is:

1. A composition for lanthionizing keratinous fibers to achieve relaxation of said keratinous fibers comprising:
   (i) at least one hydroxide compound;
   (ii) at least one reducing agent chosen from thiols, sulfites, and derivatives thereof; and
   (iii) at least one complexing agent effective for dissociating the at least one hydroxide compound in a sufficient quantity to effect lanthionization of keratinous fibers,
   wherein said at least one hydroxide compound and said at least one reducing agent are present in a combined amount effective to relax keratinous fibers, wherein said at least one reducing agent is present in an amount ranging from 0.1% to 5% by weight relative to the total weight of the composition, and
   with the proviso that if said at least one reducing agent is chosen from cysteine, cysteine derivatives, and thioglycolic acid, said at least one hydroxide compound is present in an amount such that the amount of hydroxide ion is less than 1% by weight relative to the total weight of said composition.

2. A composition according to claim 1, wherein said at least one hydroxide compound is chosen from alkali metal hydroxides, alkaline earth metal hydroxides, transition metal hydroxides, lanthanide metal hydroxides, actinide metal hydroxides, Group Ill hydroxides, Group IV hydroxides, Group V hydroxides, Group VI hydroxides, organic hydroxides, and compounds comprising at least one hydroxide substituent which is at least partially hydrolyzable.

3. A composition according to claim 2, wherein said at least one hydroxide compound is chosen from sodium hydroxide, lithium hydroxide, and potassium hydroxide.

4. A composition according to claim 3, wherein said at least one hydroxide compound is sodium hydroxide.

5. A composition according to claim 1, wherein said at least one hydroxide compound is present in an amount such that the amount of hydroxide ion ranges from 0.05% to 3% by weight relative to the total weight of said composition.

6. A composition according to claim 5, wherein said at least one hydroxide compound is present in an amount such that the amount of hydroxide ion ranges from 0.1% to 1% by weight relative to the total weight of said composition.

7. A composition according to claim 1, wherein said thiols are chosen from thioglycolates, thiolactates, thiolglycerols, thiocarboxylic acids, thioesters, thioamides, alkyl mercaptans, and cysteine.

8. A composition according to claim 7, wherein said at least one reducing agent is chosen from thioglycolates.

9. A composition according to claim 8, wherein said thioglycolates are ammonium thioglycolate.

10. A composition according to claim 1, wherein said sulfites are chosen from hydrogen sulfite, organic sulfites and inorganic sulfites.

11. A composition according to claim 1, further comprising at least one cation exchange composition.

12. A composition according to claim 11, wherein said at least one cation exchange composition is chosen from clays.

13. A composition according to claim 11, wherein said at least one cation exchange composition is chosen from silicates.

14. A composition according to claim 13, wherein said silicates are chosen from analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate.

15. A composition according to claim 13, wherein said silicates are chosen from zeolites.

16. A composition according to claim 13, wherein said silicates are chosen from zeolite clays.

17. A composition according to claim 1, further comprising at least one solvent.

18. A composition according to claim 17, wherein said at least one solvent is chosen from DMSO and water.

19. A composition according to claim 1, wherein said at least one complexing agent is chosen from chelating agents, sequestering agents and salts of any of the foregoing.

20. A composition according to claim 1, wherein said dissociation is chosen from partial dissociation and full dissociation.

21. A composition according to claim 1, wherein at least one entity chosen from said least one hydroxide compound and said at least one complexing agent is formulated with at least one reducing agent.

22. A composition according to claim 19, wherein said chelating agents are chosen from ethylene-diaminetetraacetic acid (EDTA), nitrolotriacetic acid and ethylenegylcol-bis (β-amino-ethyl ether)-N,N-tetraacetic acid.

23. A composition according to claim 19, wherein said sequestering agents are chosen from hydroxy carboxylic acids.

24. A composition according to claim 23, wherein said hydroxy carboxylic acids are chosen from gluconic acid, citric acid and tartaric acid.

25. A composition according to claim 19, wherein said at least one complexing agent is chosen from amino acids and crown ethers.

26. A composition according to claim 25, wherein said amino acids are monosodium glutamate.

27. A composition according to claim 19, wherein said at least one complexing agent is chosen from phosphates demonstrating chelating properties, phosphates demonstrating sequestering properties, phosphonates demonstrating chelating properties, phosphonates demonstrating sequestering properties, silicates demonstrating chelating properties and silicates demonstrating sequestering properties.

28. A composition according to claim 27, wherein said at least one complexing agent is chosen from tripotassium phosphate and trisodium phosphate.

29. A composition according to claim 27, wherein said at least one complexing agent is chosen from disodium silicate and dipotassium silicate.

30. A composition according to claim 1, wherein said at least one complexing agent is chosen from organic acids and salts thereof.

31. A composition according to claim 1, wherein said at least one complexing agent is chosen from mono-hydroxycarboxylic acids, dihydroxycarboxyl ic acids, polyhydroxycarboxylic acids, mono-aminocarboxylic acids, di-aminocarboxylic acids, poly-aminocarboxylic acids, monohydroxysulfonic acids, di-hydroxysulfonic acids, polyhydroxysulfonic acids, mono-hyd roxyphosphonic acids, dihyd roxyphosphonic acids, polyhydroxyphosphonic acids, mono-aminophosphonic acids, diaminophosphonic acids and polyaminophosphonic acids.

32. A composition according to claim 1, wherein said at least one complexing agent is chosen from ethylene diamine tetraacetic acid (EDTA), N-(hydroxyethyl) ethylene diamine triacetic acid, aminotrimethylene phosphonic acid, diethylenetriamine-pentaacetatic acid, lau royl ethylene diamine triacetic acid, nitrilotriacetic acid, iminodisuccinic acid, tartaric acid, citric acid, N-2-hydroxyethyliminodiacetic acid and salts of any of the foregoing.

33. A composition according to claim 32, wherein said at least one complexing agent is chosen from sodium EDTA, lithium EDTA, potassium EDTA and guanidine EDTA.

34. A composition according to claim 1, wherein said at least one complexing agent and said at least one hydroxide compound form at least one complexing agent-counter ion complex.

35. A composition according to claim 1, wherein said composition comprises at least two complexing agents.

36. A composition according to claim 1, further comprising at least one additive chosen from dyes, anionic surfactants, cationic surfactants, nonionic surfactants, amphoteric su rfactants, fragrances, silicones, silicone derivatives, screening agents, preserving agents, proteins, vitamins, polymers, plant oils, mineral oils and synthetic oils.

37. A composition according to claim 1, wherein said composition is in a form chosen from an oil-in-water emulsion, a water-in-oil emulsion, a dispersion, a suspension, a cream, a foam, a gel, a spray, a powder and a liquid.

38. A composition according to claim 1, wherein said keratinous fibers is chosen from hair.

39. A composition according to claim 1, wherein said composition is heat-activated.

40. A composition for lanthionizing keratinous fibers to achieve relaxation of said keratinous fibers comprising:
(i) at least one hydroxide compound;
(ii) at least one reducing agent chosen from thiols, sulfites, and derivatives thereof; and
(iii) at least one complexing agent effective for dissociating the at least one hydroxide compound in a sufficient quantity to effect lanthionization of keratinous fibers,
wherein said at least one hydroxide compound and said at least one reducing agent are present in a combined amount effective to relax keratinous fibers,
wherein said at least one reducing agent is Dresent in an amount ranging from 0.1% to 5% by weight relative to the total weight of the composition, and
wherein said at least one hydroxide compound is present in an amount such that the amount of hydroxide ion ranges from 0.1% to 1% by weight relative to the total weight of said composition.

* * * * *

UNITED STATES PATENT AND TRADEMARK OFFICE
CERTIFICATE OF CORRECTION

PATENT NO. : 7,195,755 B2
APPLICATION NO. : 09/931912
DATED : March 27, 2007
INVENTOR(S) : Nghi Van Nguyen et al.

It is certified that error appears in the above-identified patent and that said Letters Patent is hereby corrected as shown below:

In claim 2, column 12, line 51, "Group Ill" should read --Group III--.

In claim 31, column 14, line 6, "dihydroxycarboxyl ic" should read --dihydroxycarboxylic--.

In claim 31, column 14, line 10, "mono-hyd roxyphosphonic" should read --mono-hydroxyphosophonic--.

In claim 31, column 14, line 11, "dihyd roxyphosphonic" should read --dihydroxyphosphonic--.

In claim 32, column 14, line 18, "lau royl" should read --lauroyl--.

In claim 36, column 14, line 34, "su rfactants," should read --surfactants,--.

In claim 40, column 14, line 58, "Dresent" should read --present--.

Signed and Sealed this

Twenty-ninth Day of May, 2007

JON W. DUDAS
*Director of the United States Patent and Trademark Office*